(12) United States Patent
Ostrow

(10) Patent No.: US 6,371,946 B1
(45) Date of Patent: Apr. 16, 2002

(54) MEDICATION DISPENSING SYSTEM

(75) Inventor: Alvin S. Ostrow, Ra'anana (IL)

(73) Assignee: Electromagnetic Bracing Systems, Inc., West Trenton, NJ (US)

( * ) Notice: Subject to any disclaimer, the term of this patent is extended or adjusted under 35 U.S.C. 154(b) by 0 days.

(21) Appl. No.: 09/549,048

(22) Filed: Apr. 13, 2000

Related U.S. Application Data

(63) Continuation of application No. 09/002,425, filed on Jan. 2, 1998, now Pat. No. 6,053,898.

(51) Int. Cl.[7] .......................... A61M 35/00; B67D 5/64
(52) U.S. Cl. ................. 604/310; 604/292; 222/175
(58) Field of Search ..................... 222/75, 78, 175, 222/192, 389; 234/529, 322; 446/473, 483; 604/289, 290, 292, 310, 19, 26, 37

(56) References Cited

U.S. PATENT DOCUMENTS

| | | | | | |
|---|---|---|---|---|---|
| 1,533,732 A | * | 4/1925 | Frost | ........................... | 239/549 |
| 2,132,459 A | * | 10/1938 | Cockcroft | .................... | 239/529 |
| 4,037,790 A | * | 7/1977 | Reiser et al. | ................ | 239/529 |
| 4,903,864 A | * | 2/1990 | Sirhan | ......................... | 222/78 |
| 4,997,110 A | * | 3/1991 | Swenson | .................... | 222/175 |
| 5,045,073 A | * | 9/1991 | Wagner | ...................... | 604/310 |
| 5,303,847 A | * | 4/1994 | Cottone | ...................... | 222/175 |
| 5,484,085 A | * | 1/1996 | Bennett | ...................... | 222/175 |
| 5,538,164 A | * | 7/1996 | Rivas | .......................... | 222/175 |

* cited by examiner

Primary Examiner—Kim M. Lewis
(74) Attorney, Agent, or Firm—William Nitkin

(57) ABSTRACT

A medication dispensing system and method utilizing a dispensing tube on a therapist's hand for receiving medicated and non-medicated fluids, lotions and gels from a reservoir to be disposed onto a patient by manual contact by the therapist is disclosed.

1 Claim, 5 Drawing Sheets

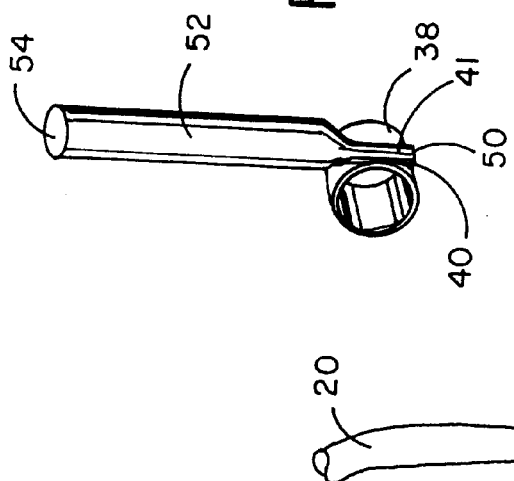
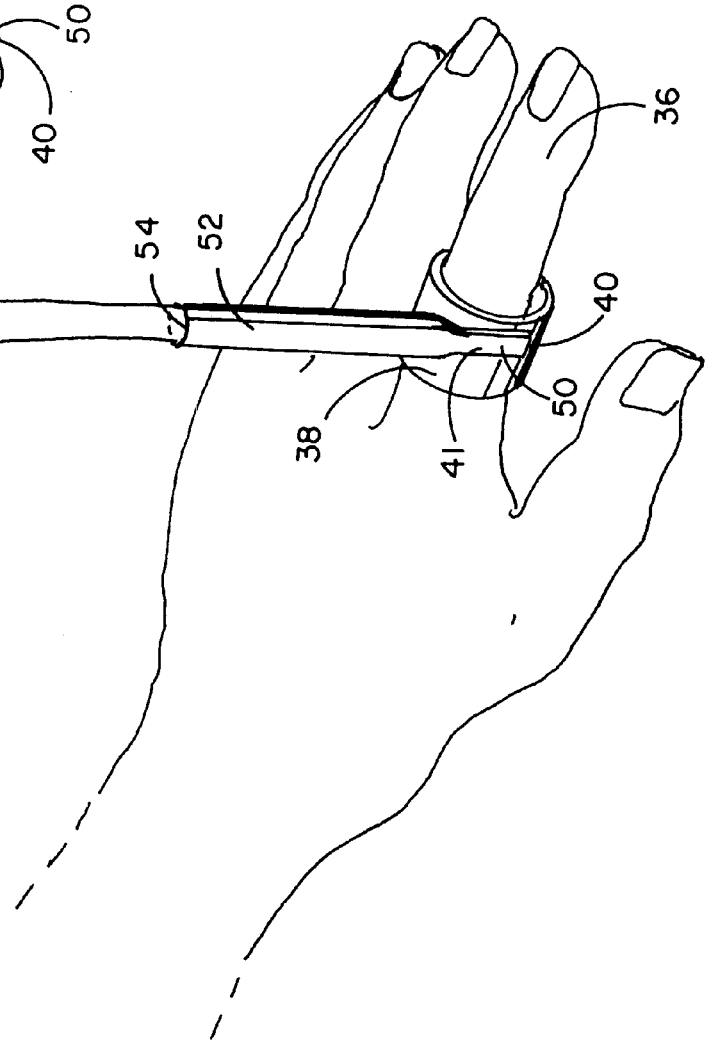

MEDICATION DISPENSING SYSTEM

This application is a continuation of my earlier filed application under the same title, Ser. No. 09/002,425 filed Jan. 1, 1998, now pending, now U.S. Pat. No. 6,053,898.

BACKGROUND OF THE INVENTION

1. Field of the Invention

This invention resides in the field of fluid dispensers and more particularly relates to a medical treatment system where medicated and non-medicated fluids, lotions, gels and the like are delivered through a delivery tube for application on a patient.

2. Description of the Prior Art

Traditionally, clinicians, physical therapists and medical personnel have applied lotion to a patient by squeezing an appropriate amount from a container onto their hand and then have applied such lotion manually directly to the patient's skin. Lotion dispensing containers, many of which work by compressing the container to squeeze out the lotion, are known in the prior art. Examples include U.S. Pat. No. 5,476,194 to Hippely et al which describes a flexible dispenser which can be worn around a person's neck; and U.S. Pat. No. 4,657,159 to Grant which discloses a meniscus-shaped container. One disadvantage of these types of containers is that a therapist must go back and forth between obtaining lotion from the container and applying it to the patient, wasting valuable time. There is also the potential for contamination if the therapist's hands carry germs from the patient to the container or if excess lotion originally removed from the container is replaced back in the container when not needed.

Other types of lotion-dispensing devices often include a container housing the lotion with some type of applicator at the end, where the applicator contacts a patient's skin after becoming saturated with lotion. Examples include U.S. Pat. No. 5,322,382 to Hull et al and U.S. Pat. No. 4,889,441 to Tice. With these types of devices the therapist has difficulty controlling the delivery of lotion to the patient's skin and must stop the therapy, such as a massage, to apply the lotion.

Hand-held spray devices often appear in children's toys. U.S. Pat. No. 5,303,847 to Cottone discloses a water toy worn on a user's hand which includes a targeting finger sheath having a discharge nozzle for spraying water. An actuating finger sheath worn on another finger controls operation of an electric motor and water pump which pumps water contained in a housing through a pipe and out the nozzle on the targeting finger sheath. U.S. Pat. No. 4,037,790 describes a water glove toy which expels water from an area near the wrist by pressing on a compressible bulb at the palm portion of the glove.

SUMMARY OF THE INVENTION

It is an object of the medication delivery system of this invention to provide a constant flow of a fluid, such as a medicated lotion or gel, through a delivery tube on the therapist's hand for an efficient and controlled dispensing of the medication for the therapist to spread onto the skin of a patient, as desired.

It is a further object of this invention to provide a medication delivery system where the medication is released through a delivery tube in doses controlled by a therapist.

It is a yet further object of this invention to provide a medication delivery system for efficiently dispensing a medication in a timesaving manner.

It is a still further object of this invention to provide a dispenser and applicator which are disposable after use by each patient so that the same container of lotion can be utilized in the care of many patient's without fear of cross-contamination.

BRIEF DESCRIPTION OF THE DRAWINGS

FIG. 3 illustrates an alternate embodiment of the medication delivery system shown in FIG. 2 including a wrist strap and an alternate embodiment of the ring applicator.

FIG. 4 illustrates a perspective front view of the ring applicator shown in FIG. 3.

DESCRIPTION OF THE PREFERRED EMBODIMENT(S)

Figure 1:
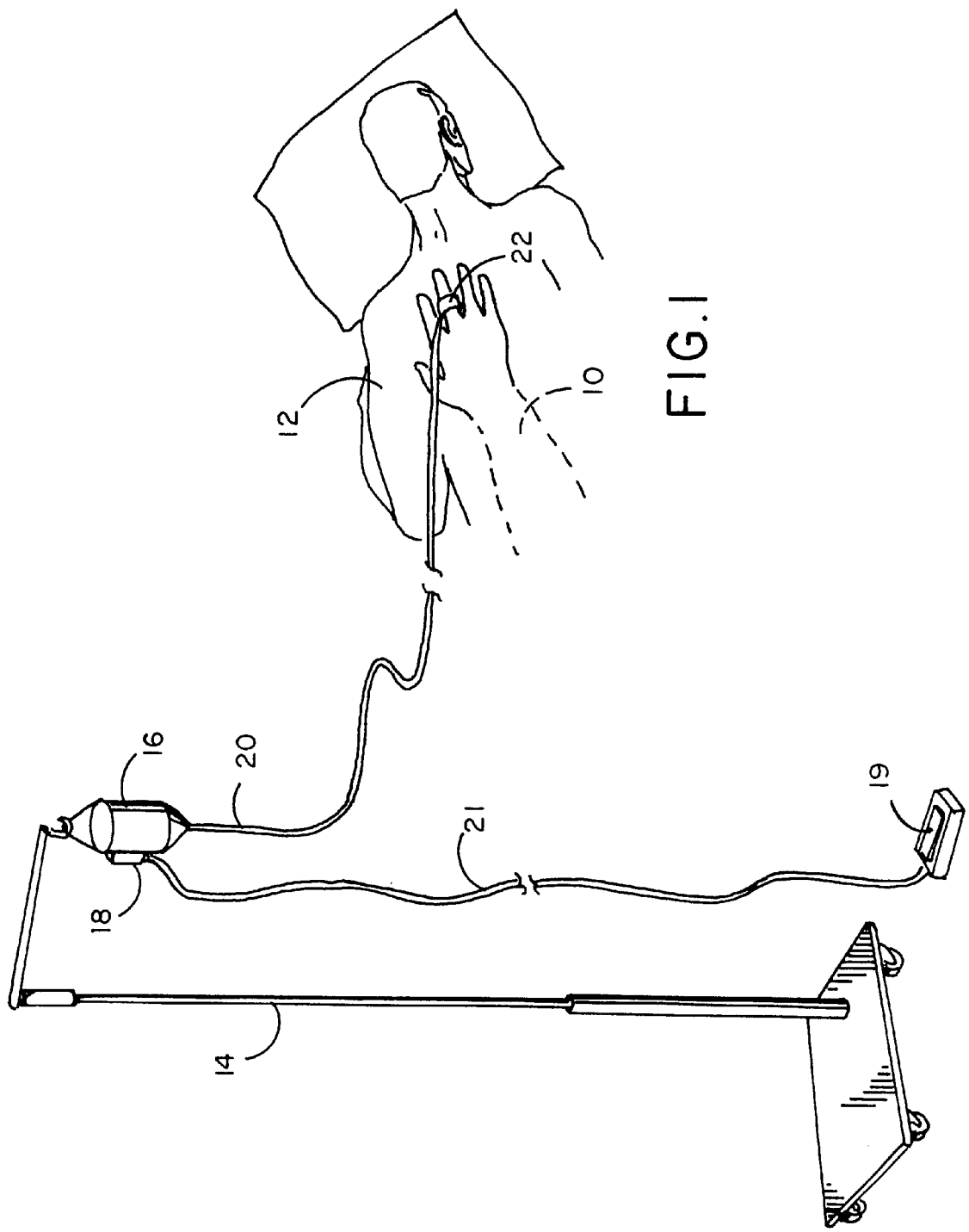
FIG. 1 illustrates a perspective view of the hand of a therapist utilizing one embodiment of the medication delivery system of this invention to apply fluid medication to a patient.

FIG. 1 illustrates a perspective view of one embodiment of the medication delivery system of this invention. Seen in this view is the hand of therapist 10 or other health care professional, hereinafter referred to as therapist applying a fluid, lotion, gel or medication, hereinafter all referred to as medication, to patient 12. Therapist 10 is wearing on one finger a ring applicator 22 through which the medication is dispensed. A stand 14 supports medication reservoir 16 which contains the medication in the form of a lotion, gel or other fluid. Delivery tube 20 runs from reservoir 16 to ring applicator 22, carrying the medication from the reservoir to ring applicator 22. Tube 20 can be either flexible or rigid with bendable sections. Due to the pumping action hereinafter described, the medication only moves in one direction through delivery tube 20, thereby preventing any germs from traveling back up the tube and thereby avoiding any cross-contamination.

The therapist can control the flow of medication being dispensed through the ring applicator to patient 12 by applying pressure to foot pump 19 or by using other well-known non-manual actuation means. Pump line 21 runs from foot pump 19 to pump 18, thereby actuating pump 18 to pump medication through delivery tube 20. The foot pump illustrated in FIG. 1 requires no electricity but could alternatively be replaced by an electric pump controlled by various well known means of actuation. Pump 18 can be any suitable commercially available pump.

Figure 2:
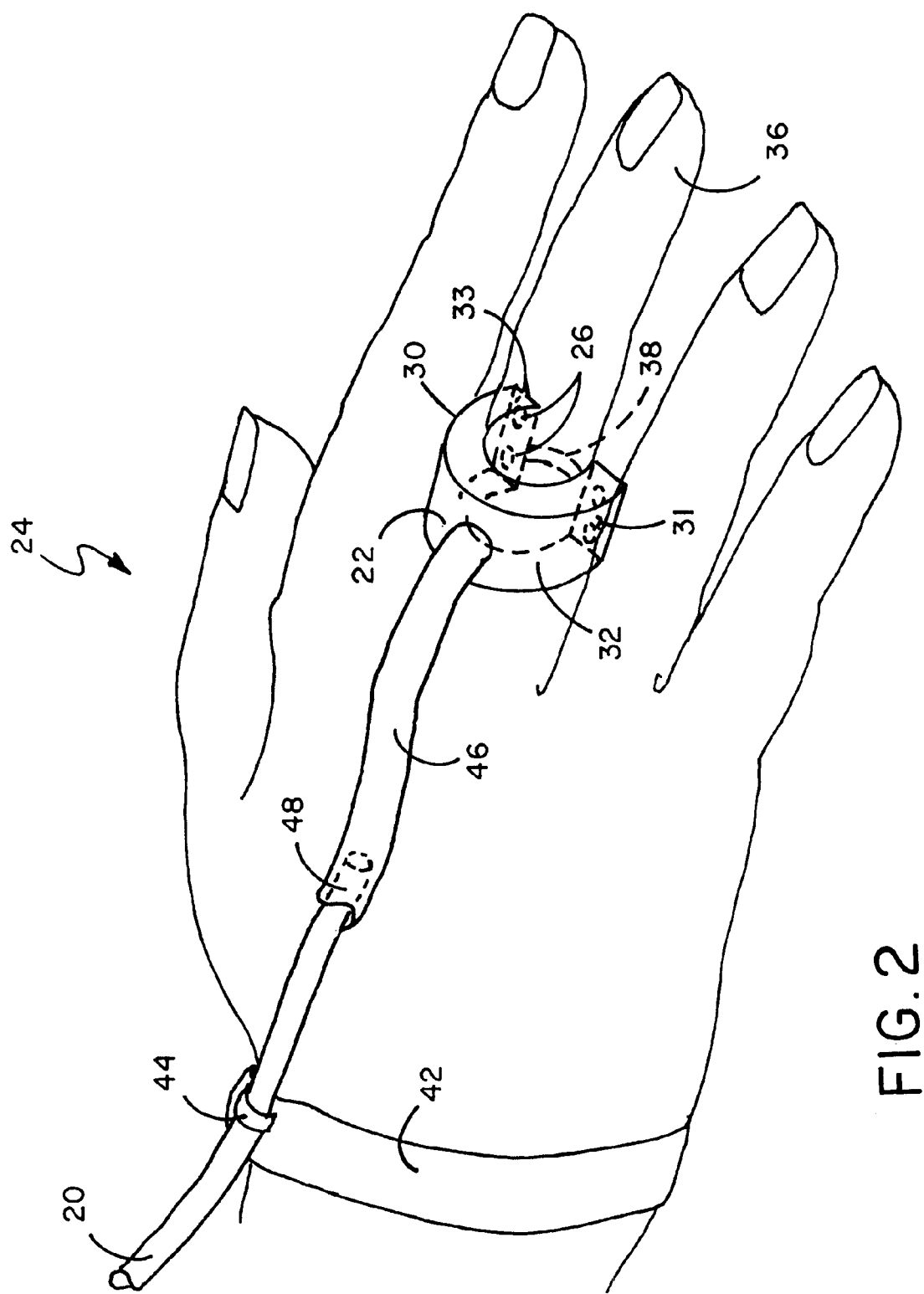
FIG. 2 illustrates an enlarged perspective view of a therapist's hand with ring applicator worn on a finger.

FIG. 2 illustrates an enlarged view of ring applicator 22 worn on a therapist's hand 24. Ring applicator 22 is a generally C-shaped, hollow structure having a first side 30 and second side 32 and at least one aperture 26 defined therein through which the medication exits. In a preferred embodiment hollow ring applicator 22 can communicate through tube segment 48 connected in fluid-tight relationship to the end of delivery tube 20. Ring applicator 22 extends in a semicircular fashion around the sides of the finger on which it is worn. First side 30 and second side 32 of ring applicator 22 in a preferred embodiment can have multiple apertures 26 defined at its ends 31 and 33 through which apertures is released medication to the bottom of hand 24 or onto the patient for spreading over a patient's skin. Ring applicator 22 can be held on the therapist's finger by retention band 38 which connects first side 30 to second side 32 or by equivalent attachment means. Ring applicator 22 and the various parts thereof including in one embodiment tube segment 48 can be disposable to ensure no cross-contamination occurs during treatment of different patients. The ring applicator and tube segment can be made of plastic and in an one embodiment can be produced as a single molded disposable unit. As seen in this view, wrist strap 42 is secured around the clinician's wrist and tube 20 is held by hook 44. Wrist strap 42 reduces possible injury to the therapist's finger, as any abrupt jerk of delivery tube 20 will be directed to the wearer's wrist instead of to finger 36.

FIG. 3 illustrates an alternate embodiment of the medication delivery system of this invention being an alternate embodiment of the ring applicator which in this view is being worn on the therapist's index finger. Instead of being semicircular in shape, band 38 extends entirely around finger 36. Applicator extension 52, having first end 54 and second end 50, is hollow and at its first end is of a size to fit snugly around the end of delivery tube 20 in fluid-tight relationship. At the second end of applicator extension 52 has a flattened area 41 having an opening 40 therein through which the medication is dispensed. Applicator extension 52 can be attached to band 38 by glue or equivalent attachment means. The applicator extension and the band can also be molded as a one-piece unit which can be easily disposed of after use on each patient. As seen in FIG. 3 applicator extension 52 extends over the side of finger 36 that is adjacent to the thumb. Flattened area 41 does not interfere with movement of the therapist's fingers during manual therapy. The applicator extension can also be comfortably positioned to the outside of the little finger as well as between the finger's of the therapist.

Figure 5:
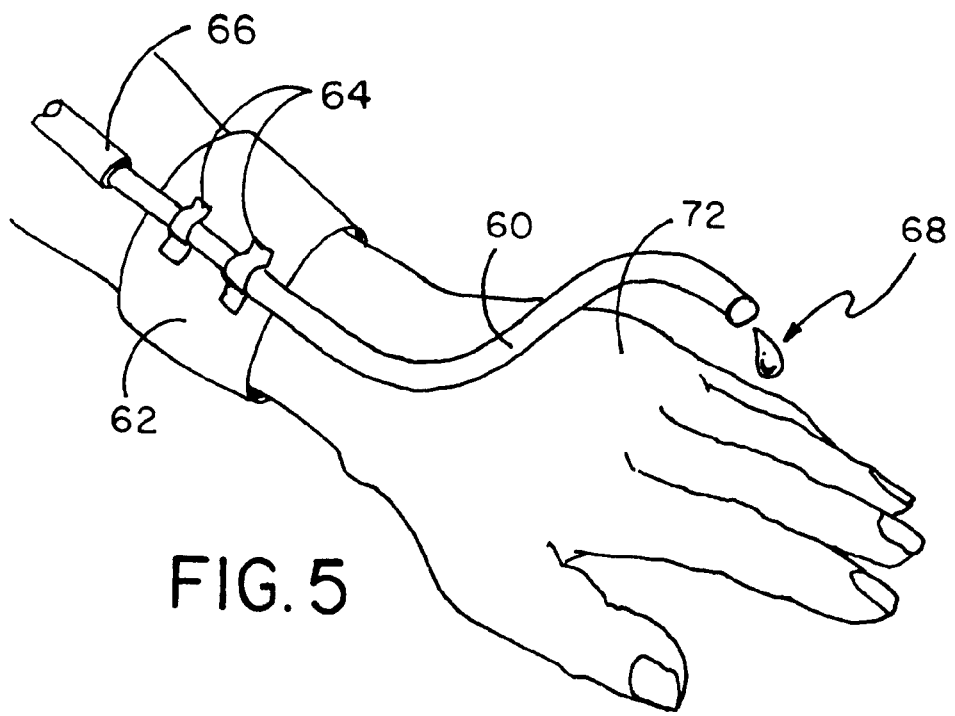
FIG. 5 illustrates a perspective view of an alternate embodiment of the medication delivery system of this invention showing a delivery tube positioned to the left of the therapist's hand.
Figure 6:
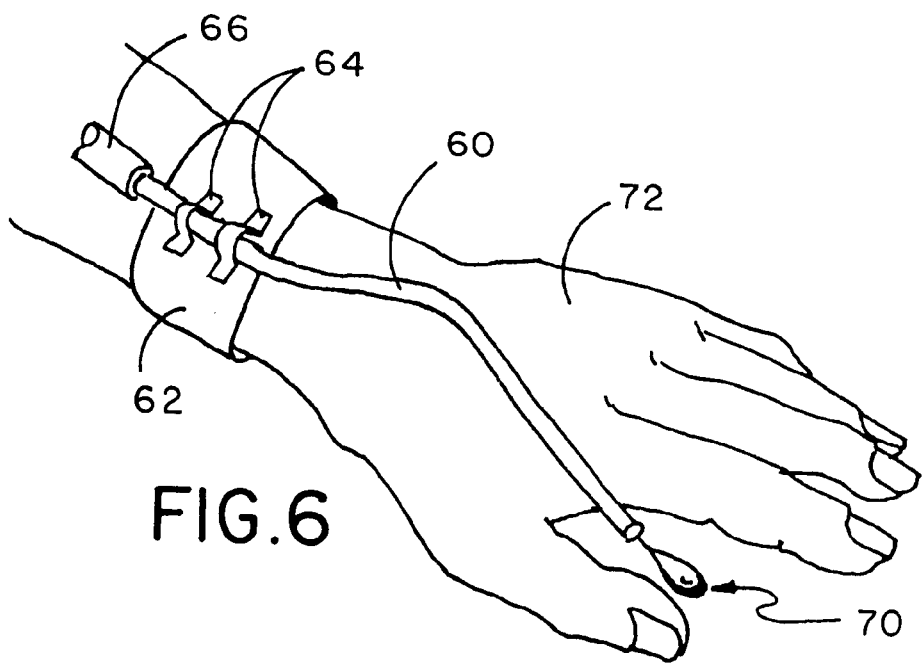
FIG. 6 illustrates a perspective view of the embodiment of FIG. 5 wherein the delivery tube has been bent to deliver a medication to the right of the therapist's hand.

In an alternate embodiment seen in FIGS. 5 and 6 a rigid yet positionable delivery tube 60, which maintains whatever shape to which it is manually bent, is utilized to deliver the medication. As seen in FIG. 5, positionable delivery tube 60 has been bent to dispense medication from its medication dispensing end to area 68 to the left of the therapist's hand 72. Positionable delivery tube 60 is securely attached by clips 64 to wrist cuff 62 which holds one end of positionable delivery tube 60 securely in place. Wrist cuff 62 must be tightened on the therapist's wrist an amount sufficient to hold cuff 62 in place and prevent its rotation. Attached to the medication receiving end of positionable delivery tube 60 is feed line 66 which extends up to the medication reservoir, not seen in this view.

Figure 7:
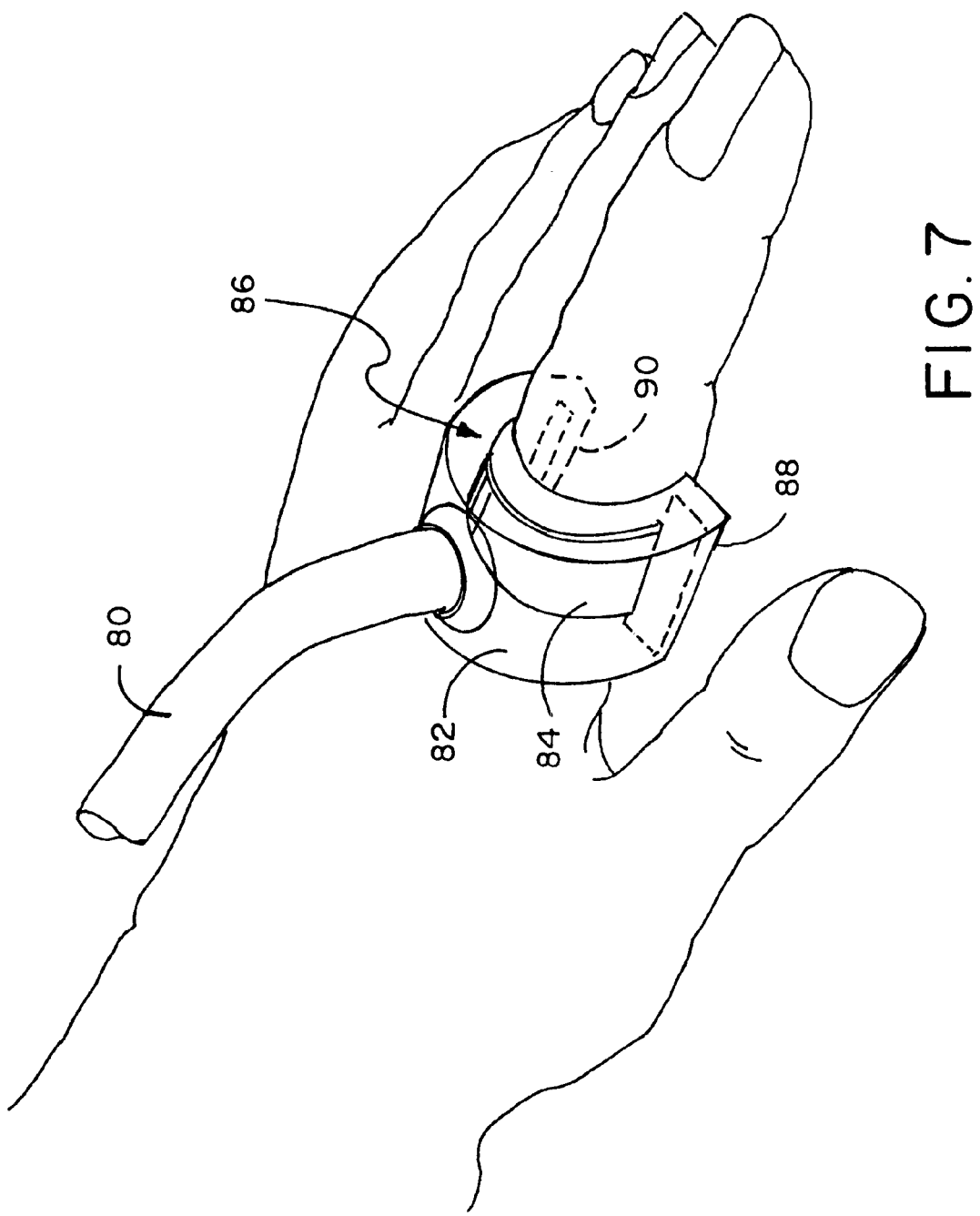
FIG. 7 illustrates a perspective view of an alternate embodiment of a ring applicator to receive and deliver a medication.

FIG. 7 illustrates yet a further embodiment of the medication delivery system of this invention with flexible ring applicator 82 which can be made of flexible material such as plastic or rubber. Flexible ring applicator 82 has positioned at its inner circumference a curved spring member 84 which fits snugly around the therapist's finger. Spring member 84 can be made of spring metal or equivalent and can be within or adhered to the inner wall of flexible ring applicator 82. When medication enters ring chamber 86 of flexible ring applicator 82, the medication causes the flexible material to expand, such as to the position seen in FIG. 7, to allow passage of the medication from pipe 80 to pass out openings 88 and 90 onto the patient. When medication is not passing through pipe 80, the flexible material of the flexible ring applicator collapses inward, and the sides of the applicator flatten so that it takes up much less space between the therapist's fingers and is thus more comfortable for the therapist to wear, expanding only when medication is pumped therethrough.

Although the present invention has been described with reference to particular embodiments, it will be apparent to those skilled in the art that variations and modifications can be substituted therefore without departing from the principles and spirit of the invention.

I claim:

1. A medication delivery system for use by a therapist applying medication to a patient, said therapist having a hand with fingers and a wrist, comprising:

a reservoir holding a medication;

a positionable delivery tube having a first end and a second end;

means to attach said first end of said delivery tube securely to said therapist's wrist, said delivery tube bendable to a selected position for disposition adjacent to, or between, said therapist's fingers;

means to connect said reservoir to said first end of said positionable delivery tube; and means for delivering said medication from said reservoir, through the connection means, through the delivery tube and onto said patient.

* * * * *